US012755830B2

(12) United States Patent
Park et al.

(10) Patent No.: US 12,755,830 B2
(45) Date of Patent: Oct. 6, 2026

(54) DEVICE FOR SETTING COORDINATES FOR EACH PART OF ORGAN OF HUMAN BODY AND METHOD OF OPERATING THE SAME

(71) Applicant: HUTOM INC., Seoul (KR)

(72) Inventors: Seok Rae Park, Gwangmyeong-si (KR); Keun Young Kim, Seoul (KR); Kyung Yoon Jung, Seoul (KR); Bo Kyoung Park, Seoul (KR)

(73) Assignee: HUTOM INC., Seoul (KR)

( * ) Notice: Subject to any disclaimer, the term of this patent is extended or adjusted under 35 U.S.C. 154(b) by 214 days.

(21) Appl. No.: 18/642,935

(22) Filed: Apr. 23, 2024

(65) Prior Publication Data

US 2024/0355453 A1 Oct. 24, 2024

(30) Foreign Application Priority Data

Apr. 24, 2023 (KR) ........................ 10-2023-0053140

(51) Int. Cl.
*G16H 30/20* (2018.01)
*G06T 7/50* (2017.01)

(52) U.S. Cl.
CPC ............... *G16H 30/20* (2018.01); *G06T 7/50* (2017.01); *G06T 2207/30004* (2013.01)

(58) Field of Classification Search
CPC ........ G16H 30/20; G16H 70/60; G16H 15/00; G16H 20/40; G16H 30/40; G06T 7/50; G06T 2207/30004; G06T 7/0012; G06T 7/70; G06T 2207/30092; G06T 7/73; G06T 7/62; G06T 11/20; A61B 34/20; A61B 2034/2068
See application file for complete search history.

(56) References Cited

U.S. PATENT DOCUMENTS 12,127,890 B1 * 10/2024 Gorrepati ........... A61B 1/00009
2013/0035576 A1 2/2013 O'Grady et al.
(Continued)

FOREIGN PATENT DOCUMENTS

CN 110459298 A 11/2019
JP 2005300620 A * 10/2005
(Continued)

OTHER PUBLICATIONS

Extended European Search Report issued in EP 24 17 2068.9-1122 by the European Patent Office on Sep. 20, 2024.
(Continued)

*Primary Examiner* — Qun Shen
(74) *Attorney, Agent, or Firm* — Studebaker Brackett PLLC

(57) ABSTRACT

The present disclosure relates a device for setting coordinates of each part of an organ of a human body and a method of operating the same. The device according to an embodiment of the present disclosure includes a memory, and a processor that receives organ information on the organ, sets a plurality of isolines connecting a first area corresponding to a first part constituting the organ and a second area corresponding to a second part constituting the organ, and generates organ coordinate system information including isoline information representing the plurality of isolines and the organ information.

15 Claims, 4 Drawing Sheets

(56) References Cited

U.S. PATENT DOCUMENTS

| | | | | |
|---|---|---|---|---|
| 2013/0229432 | A1 | 9/2013 | Vilsmeier | |
| 2018/0122150 | A1* | 5/2018 | Bidne | G06T 17/00 |
| 2019/0164291 | A1* | 5/2019 | Wang | G06V 10/50 |
| 2019/0347791 | A1 | 11/2019 | Fieselmann | |
| 2021/0225014 | A1* | 7/2021 | Na | G06T 7/33 |
| 2021/0290306 | A1* | 9/2021 | Ichikawa | G09B 23/285 |
| 2022/0067925 | A1 | 3/2022 | Massarwa et al. | |

FOREIGN PATENT DOCUMENTS

| | | | | |
|---|---|---|---|---|
| JP | 2015-087167 | A | 5/2015 | |
| JP | 2022-041995 | A | 3/2022 | |
| KR | 10-2011-0058903 | A | 6/2011 | |
| KR | 10-2498706 | B1 | 2/2023 | |
| WO | WO-2015029135 | A1 * | 3/2015 | G16H 30/20 |
| WO | WO-2024121067 | A1 * | 6/2024 | G06T 7/30 |

OTHER PUBLICATIONS

Papenkort, Stefan, et al.; "A geometry model of the porcine stomach featuring mucosa and muscle layer thicknesses"; Journal of the Mechanical Behavior of Biomedical Materials; vol. 142; Apr. 15, 2023; 105801, (XP093201270); Amsterdam, Netherland.

"Request for the Submission of an Opinion" Office Action issued in KR 10-2023-0053140; mailed by the Korean Intellectual Property Office on Jul. 18, 2025.

"Notice of Reasons for Refusal" Office Action issued in JP 2024-070508; mailed by the Japanese Patent Office on Mar. 25, 2025.

* cited by examiner

DEVICE FOR SETTING COORDINATES FOR EACH PART OF ORGAN OF HUMAN BODY AND METHOD OF OPERATING THE SAME

CROSS-REFERENCE TO RELATED APPLICATIONS

A claim for priority under 35 U.S.C. § 119 is made to Korean Patent Application No. 10-2023-0053140 filed on Apr. 24, 2023 in the Korean Intellectual Property Office, the entire contents of which are hereby incorporated by reference.

BACKGROUND

Embodiments of the present disclosure described herein relate to an electronic device, and more particularly, relate to a device for setting coordinates of each part of an organ of a human body and a method of operating the same.

To accurately describe a surgical operation, it is required to specify an exact position of an organ of each patient. There are names that specify organ parts, but since the corresponding organ parts correspond to a wide range, it may be difficult to specifically and accurately specify a position within the corresponding organ part. In detail, since there are differences in a feature of an organ shape or a size and shape of the organ for each patient, it is difficult to accurately describe a position of the organ part in a specific manner using general coordinates systems such as a rectangular coordinate system and a spherical coordinate system. Thus, it is required to designate the position in consideration of the feature of the organ shape or the shape or the like of the organ of each patient.

SUMMARY

Embodiments of the present disclosure provide a device that may describe an exact position of an organ of a human body through an isoline in surgery description.

The aspects of the present disclosure are not limited to the aspects described above, and those skilled in the art will clearly understand other aspects not described from the following description.

According to an embodiment, a device for setting coordinates of each part of an organ of a human body includes a memory, and a processor that receives organ information on the organ, sets a plurality of isolines connecting a first area corresponding to a first part constituting the organ and a second area corresponding to a second part constituting the organ, and generates organ coordinate system information including isoline information representing the plurality of isolines and the organ information.

According to an embodiment, a method of operating a device for setting coordinates of each part of an organ of a human body includes receiving organ information on the organ, setting a plurality of isolines connecting a first area corresponding to a first part constituting the organ and a second area corresponding to a second part constituting the organ, and generating organ coordinate system information including the organ information and isoline information on the plurality of isolines.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
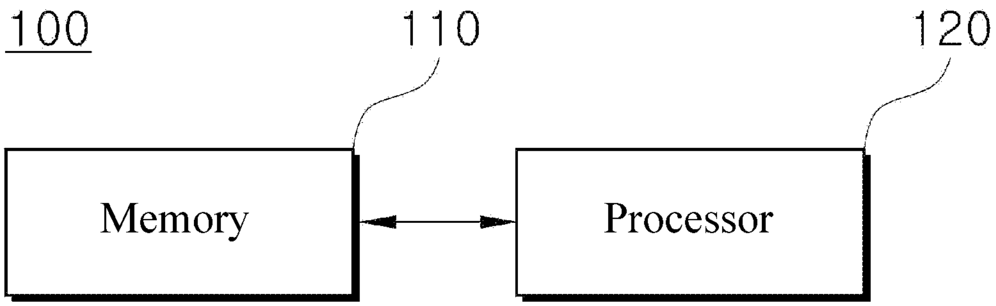
FIG. 1 is a block diagram of a device according to the present disclosure.

Throughout the present disclosure, the same reference numerals refer to the same components. The present disclosure does not describe all components of embodiments, and general contents or duplicated contents between the embodiments in the technical field to which the present disclosure pertains will be omitted. Terms "unit, module, member, and block" used in the specification may be implemented as software or hardware, and according to embodiments, a plurality of "units, modules, members, and blocks" may be implemented as a single component or one "unit, module, member, and block" may include a plurality of components.

Throughout the specification, when it is described that a first component is "connected" to a second component, this includes not only a case in which the first component is directly connected to the second component but also a case in which the first component is indirectly connected to the second component, and the indirect connection includes connection through a wireless communication network.

Further, when a part "includes" a component, this means that a third component is not excluded but may be further included unless otherwise stated.

Throughout the specification, when a first member is located "on" a second member, this case includes not only a case in which the first member is in contact with the second member but also a case in which a third member is present between the two members.

Terms such as first and second are used to distinguish a first component from a second component, and the components are not limited by the above-described terms.

Singular expressions include plural expressions unless clearly otherwise indicated in the context.

In each of operations, an identification code is used for convenience of description and does not describe a sequence of the operations, and the operations may be performed in a different order from the specified order unless the context clearly states a specific order.

Hereinafter, the operating principles and embodiments of the present disclosure will be described with reference to the accompanying drawings.

FIG. 1 is a block diagram of a device 100 according to the present disclosure.

Referring to FIG. 1, the device 100 is a device that divides each organ area to form an isoline to specify a position of an organ during surgery and provide organ coordinate system information so that a user may describe an exact position of the organ through the isoline.

The device 100 may include a memory 110 and a processor 120.

The memory 110 may store data about an algorithm for controlling operations of components inside the device and a program that reproduces the algorithm, and at least one processor 120 that performs the above-described operations using the data stored in the memory 110 may be implemented. Here, the memory 110 and the processor 120 may be implemented as separate chips. Further, the memory 110 and processor 120 may be implemented as a single chip.

The memory 110 may store data for supporting various functions of the device and a program for an operation of the processor 120, may store input/output data, and may store a number of application programs (or applications) running on the device, data for an operation of the device, and commands. At least some of these application programs may be downloaded from an external server via wireless communication.

The memory 110 may include at least one storage medium among a flash memory type memory, a hard disk type memory, a solid state disk (SSD) type memory, a silicon disk drive (SDD) type memory, a multimedia card micro type memory, a card type memory (e.g., an SD or XD memory or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. Further, the memory 110 is separate from the device, but may be a database connected by wire or wirelessly.

The processor 120 may receive organ information on an organ. The processor 120 may set a plurality of isolines connecting a first area corresponding to a first part constituting the organ and a second area corresponding to a second part constituting the organ. The processor 120 may generate organ coordinate system information including isoline information representing the plurality of isolines sand the organ information.

Although not illustrated, the device 100 may further include a communication unit capable of communicating with an external unit. In this case, the communication unit may include a wireless communication module that supports various wireless communication methods such as global system for mobile communication (GSM), code division multiple access (CDMA), wideband code division multiple access (WCDMA), an universal mobile telecommunications system (UMTS), time division multiple access (TDMA), a long term evolution (LTE), a fourth generation mobile communication (4G), a fifth generation mobile communication (5G), and a sixth generation mobile communication (6G) in addition to a Wi-Fi module and a wireless broadband module.

According to the above description, in surgical description, the exact position of the organ of a human body may be described through the isolines.

Figure 2:
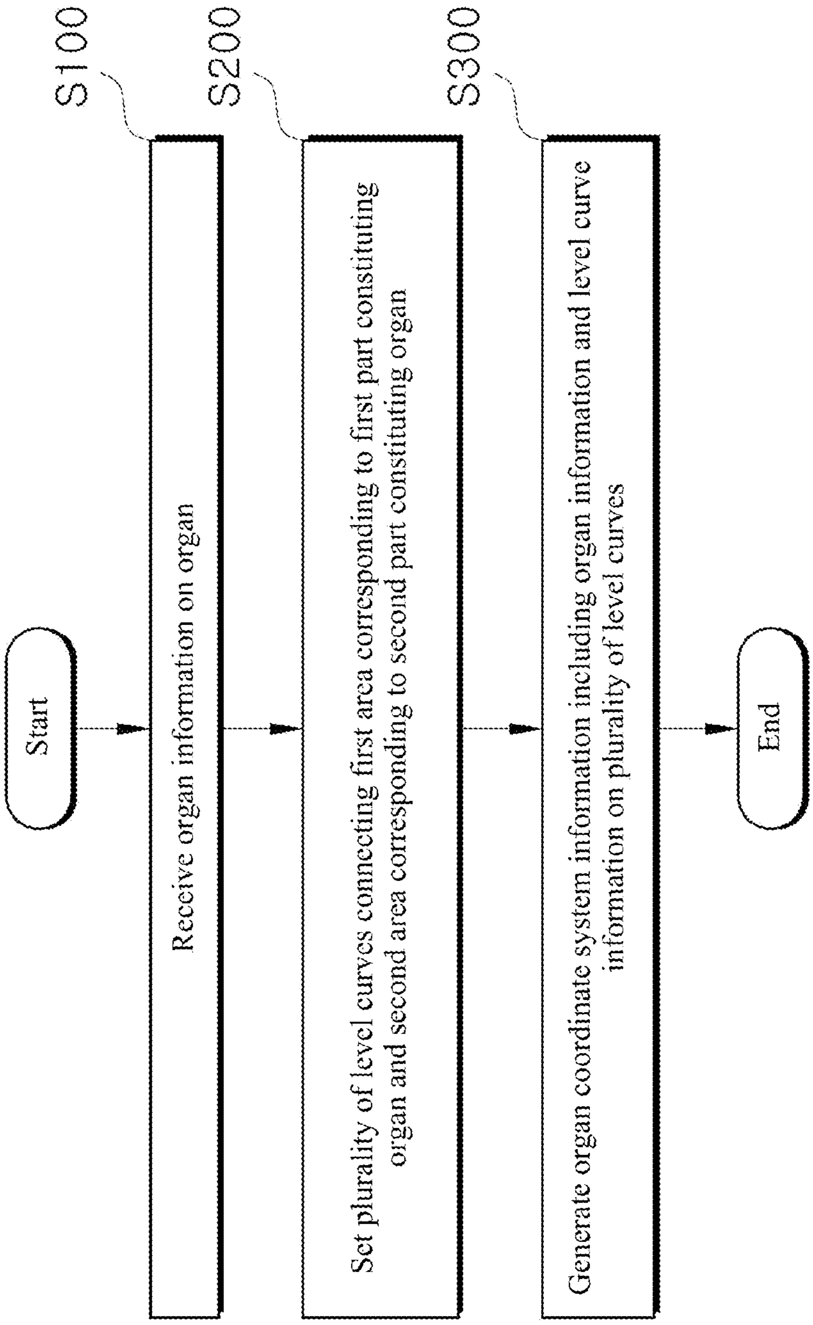
FIG. 2 is a flowchart for describing a method of operating the device according to the present disclosure.

FIG. 2 is a flowchart for describing a method of operating the device according to the present disclosure.

Referring to FIG. 2, the method of operating the device according to the present disclosure may include operation S100, operation S200, and operation S300.

In operation S100, an operation of receiving the organ information on the organ is performed.

In operation S200, an operation of setting the plurality of isolines connecting the first area corresponding to the first part constituting the organ and the second area corresponding to the second part constituting the organ is performed.

In operation S300, an operation of generating the organ coordinate system information including the organ information and the isoline information on the plurality of isolines.

According to the above description, in surgical description, the exact position of the organ of the human body may be described through the isolines.

Figure 3:
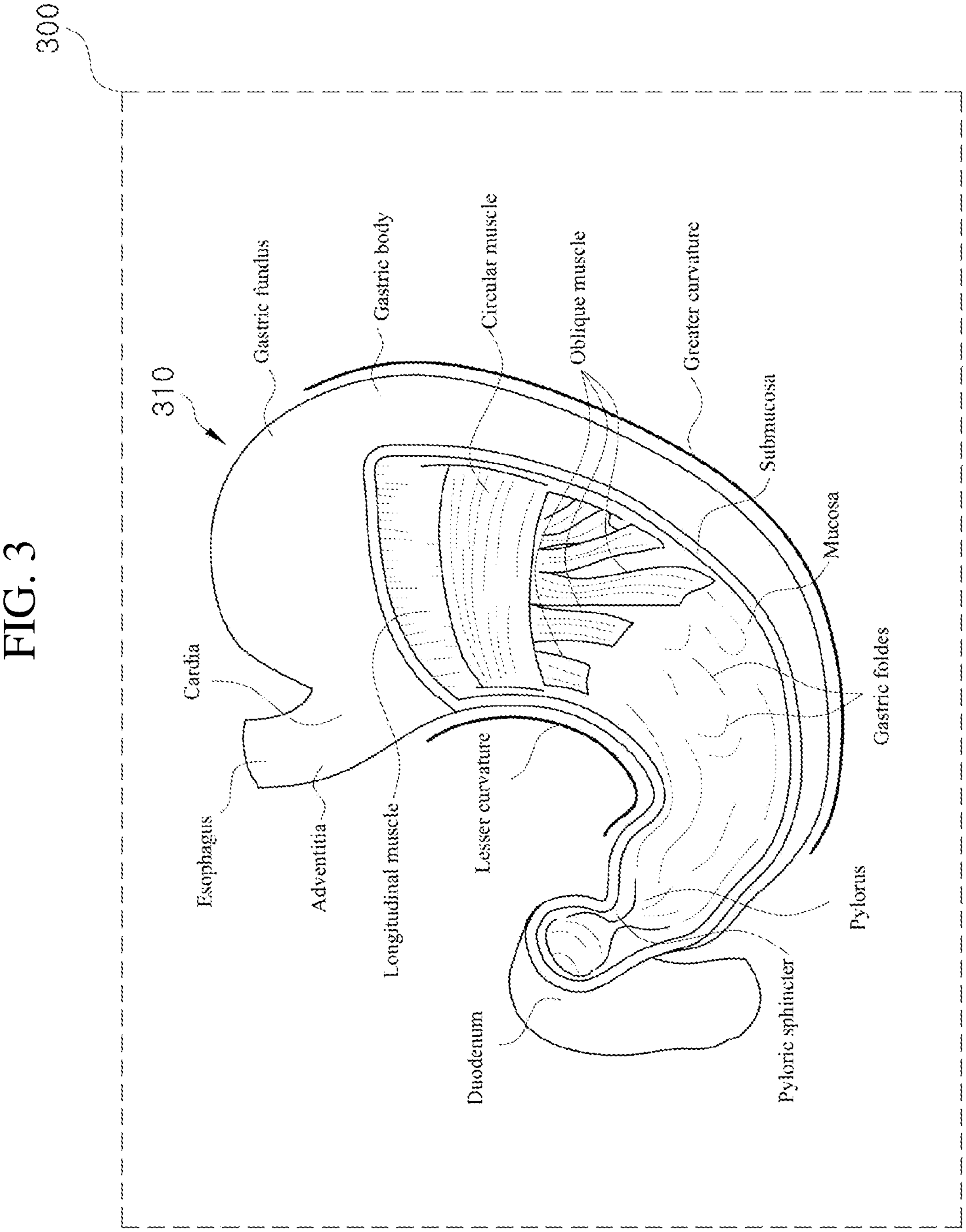
FIG. 3 is an exemplary view illustrating organ information according to the present disclosure.

FIG. 3 is an exemplary view illustrating organ information according to the present disclosure.

Referring to FIG. 3, the organ information may include an organ image 300 representing an organ 310. The organ information may include a name of the organ 310 and medical names of respective portions constituting the organ 310.

Referring to FIG. 3, for example, the organ 310 may correspond to a stomach. The name of the organ 310 may be stomach. The medical names of the respective portions of the stomach may include esophagus, adventitia, cardia, longitudinal muscle, lesser curvature, gastric fundus, gastric body, circular muscle, oblique muscle, greater curvature, gastric folds, submucosa, mucosa, pylorus, pyloric sphincter, and the like.

In some embodiments, the first part for setting the isoline may correspond to a first medical name, and the second part may correspond to a second medical name. Referring to FIG. 3, for example, the first medical name may be the lesser curvature, and the first part may be a part representing the lesser curvature. The second medical name is the greater curvature and the second part may be a part representing the greater curvature. However, the present disclosure is not limited thereto.

Figure 4:
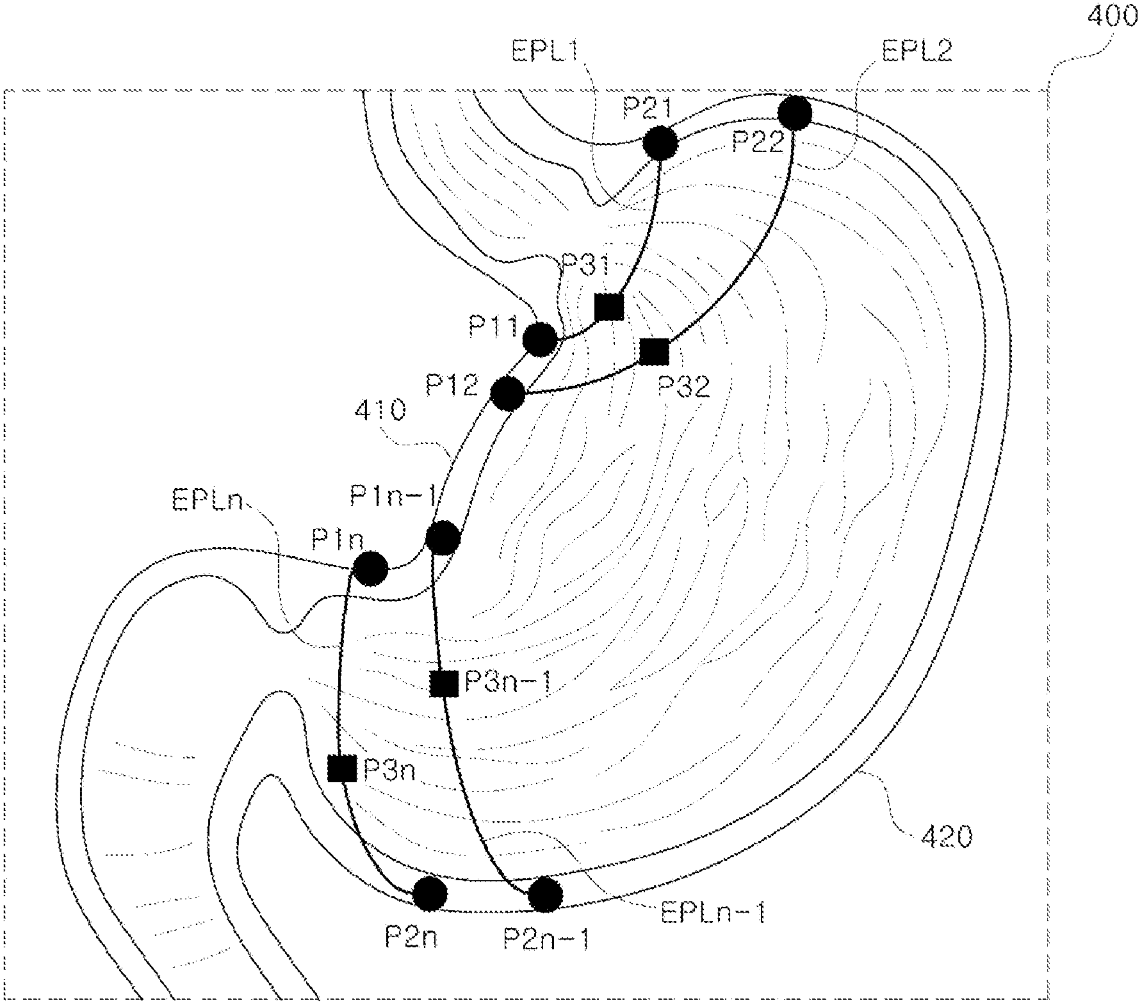
FIG. 4 is a view for describing a method of setting a plurality of isolines according to the present disclosure.

FIG. 4 is a view for describing a method of setting a plurality of isolines according to the present disclosure.

Referring to FIG. 4, an organ image 400 of FIG. 4 may be an image representing a cross-sectional view of the organ. Referring to FIG. 4, for example, the organ image 400 may include a cross-sectional view of the stomach. However, the present disclosure is not limited thereto, and the organ image 400 may represent a three-dimensional organ which is like the organ image 300 of FIG. 3.

In some embodiments, a first area 410 may correspond to the first part, and the first part may be the lesser curvature. A second area 420 may correspond to the second part, and the second part may be the greater curvature.

In some embodiments, the processor 120 may set a plurality of first points P11, P12, P1n−1, and P1n on the first area 410. The number of the plurality of first points P11, P12, P1n−1, and P1n may be n. n may be an integer of 2 or more. The processor 120 may set a plurality of second points P21, P22, P2n−1, and P2n on the second area 420. The number of the plurality of second points P21, P22, P2n−1, and P2n may be n. The processor 120 may set the plurality of isolines EPL1, EPL2, EPLn−1, and EPLn by connecting the first points and the second points positioned at the same order from the starting points to the end points of the first area 410 and the second area 420. For example, the starting point of the first area 410 may be the first point P11, and the end point of the first area 410 may be the first point P1n. For example, the starting point of the second area 420 may be the second point P21, and the end point of the second area 420 may be the second point P2n. For example, the first point and the second point positioned at a first order may be the first point P11 and the second point P21, respectively. As another example, the first point and the second point positioned at a second order may be the first point P12 and the second point P22, respectively. As still another example, the first point and the second point positioned at a $n^{th}$ order may be the first point P1n and the second point P2n, respectively. The number of the plurality of isolines EPL1, EPL2, EPLn−1, and EPLn may be n.

According to the above description, a position of an organ part may be described using the isoline formed in the divided range. By ordering the formed isolines, the user may describe the exact position using the number of the isoline during surgery. In a describing method, for example, the position of the organ part may be described by the name of the organ, an order of the isoline, a distance from a reference point of an inner line (or a reference point of an outer line) along the isoline, and the like.

In some embodiments, the plurality of isolines EPL1, EPL2, EPLn−1, and EPLn may be positioned on an inner circumferential surface corresponding to a periphery of the organ. Since the actual organ has a three-dimensional shape, the plurality of isolines EPL1, EPL2, EPLn−1, and EPLn may have a curved shape positioned along an inner circumferential surface of the three-dimensional organ. In other embodiments, the plurality of isolines EPL1, EPL2, EPLn−1, and EPLn may be positioned on an outer circumferential surface of the organ.

In some embodiments, the processor 120 may recognize a detailed area range of each organ and then divide the corresponding range at equal intervals. That is, the processor 120 may set the plurality of first points P11, P12, P1n−1, and P1n at equal intervals. Referring to FIG. 4, for example, a first interval between the plurality of first points P11, P12, P1n−1, and P1n may be the same. The processor 120 may set the plurality of second points P21, P22, P2n−1, and P2n at equal intervals. Referring to FIG. 4, for example, a second interval between the plurality of second points P21, P22, P2n−1, and P2n may be the same. That is, the processor 120 may specify an inner area (lesser curvature) and an outer area (greater curvature) of the stomach as ranges and may divide the inner area and the outer area into the same number of parts. The size of the lesser curvature and the size of the greater curvature may be different from each other. Therefore, the first interval between the plurality of first points P11, P12, P1n−1, and P1n and the second interval between the plurality of second points P21, P22, P2n−1, and P2n may be different from each other. Referring to FIG. 4, for example, when the size of the lesser curvature is smaller than the size of the greater curvature, the first interval may be smaller than the second interval. The processor 120 may sequentially set a number to each of the plurality of isolines from the isoline formed by connecting the starting points to the isoline formed by connecting the end points. For example, the isoline formed by connecting the starting points may be the first isoline EPL1, and the isoline formed by connecting the end points may be the $n^{th}$ isoline EPLn. A number may be set to each of the plurality of isolines EPL1, EPL2, EPLn−1, and EPLn sequentially form the first isoline EPL1 to the $n^{th}$ isoline EPLn. In this case, the first isoline EPL1 may be set to a first order, the second isoline EPL2 may be set to a second order, and the $n^{th}$ isoline may be set to an $n^{th}$ order.

In some embodiments, the processor 120 may calculate a separation distance from the first point or the second point positioned at the same order on the isoline formed by connecting the first point and the second point positioned at the same order. For example, a separation distance from the first point P11 or the second point P21 on the first isoline EPL1 formed by connecting the first point P11 and the second point P21 positioned at the first order may be calculated. The processor 120 may obtain a third point positioned at a distance spaced apart from the first point or the second point positioned at the same order. For example, the processor 120 may acquire a third point P31 that is spaced apart from the first point P11 (or the second point P21) on the first isoline EPL1. As another example, a third point P32 may be obtained on the second isoline EPL2, a third point P3n−1 may be obtained on the $(n-1)^{th}$ isoline EPLn−1, and a third point P3n may be obtained on the $n^{th}$ isoline EPLn. The processor 120 may generate the organ coordinate system information that further includes point information representing the plurality of first points P11, P12, P1n−1, and P1n, the plurality of second points P21, P22, P2n−1, and P2n, and at least one third point. Accordingly, coordinates of the position of the organ part positioned on the isoline may be obtained.

Meanwhile, the disclosed embodiments may be implemented in the form of a recording medium that stores a computer-readable command. The command may be stored in the form of a program code, and when the command is executed by a processor, a program module may be generated to perform operations of the disclosed embodiments. The recording medium may be implemented as a computer-readable recording medium.

The computer-readable recording medium includes all types of recording media storing commands that may be decoded by a computer. Examples of the computer-readable recording medium may include the ROM, the RAM, a magnetic tape, a magnetic disk, a flash memory, an optical data storage device, and the like.

According to the above description, in surgical description, an exact position of an organ of a human body may be described through an isoline.

Those skilled in the art to which the present disclosure pertains may understand that the present disclosure may be implemented in forms different from the disclosed embodiments without changing the technical spirit or essential feature of the present disclosure. The disclosed embodiments are illustrative and should not be construed restrictively.

What is claimed is:

1. A device for setting coordinates of each part of an organ of a human body, the device comprising:

a memory; and a processor configured to receive organ information on the organ, set a plurality of isolines connecting a first area corresponding to a first part constituting the organ and a second area corresponding to a second part constituting the organ, and generate organ coordinate system information including isoline information representing the plurality of isolines and the organ information, wherein the processor is further configured to:

set a plurality of first points at equal intervals from a first start point to a first end point on the first area;

assign sequential numbers to the plurality of first points from the first start point to the first end point;

set a plurality of second points at equal intervals from a second start point to a second end point on the second area;

assign sequential numbers to the plurality of second points from the second start point to the second end point; and set the plurality of isolines by connecting the first points and the second points having the same assigned numbers, wherein the organ coordinate system information is configured to enable a position of the organ to be described in a standardized manner using the plurality of isolines despite differences in shape of the organ among different patients, and wherein the organ information includes a name of the organ and medical names of respective parts constituting the organ.

2. The device of claim 1, wherein the processor is configured to:

set a plurality of first points on the first area; and set a plurality of second points on the second area, and wherein the plurality of isolines are set by connecting the first point and the second point positioned at the same order from staring points to end points of the first area and the second area.

3. The device of claim 2, wherein the processor is configured to:

set the plurality of first points at equal intervals; and set the plurality of second points at equal intervals, and wherein a number is set to each of the plurality of isolines sequentially from an isoline formed by connecting the starting points to an isoline formed by connecting the end points.

4. The device of claim 3, wherein the processor is configured to:

calculate a distance spaced apart from the first point or the second point positioned at the same order on an isoline formed by connecting the first point and the second point positioned at the same order;

acquire a third point positioned at the distance spaced apart from the first point or the second point positioned at the same order; and generate the organ coordinate system information further including point information representing the plurality of first points, the plurality of second points, and the third point.

5. The device of claim 4, wherein the plurality of isolines are positioned on an inner circumferential surface corresponding to a periphery of the organ.

6. The device of claim 5, wherein the organ information includes an organ image representing the organ.

7. The device of claim 6, wherein the organ information includes a name of the organ and medical names of respective parts constituting the organ, wherein the first part corresponds to a first medical name, wherein the second part corresponds to a second medical name, wherein the organ corresponds to a stomach, wherein the first medical name includes a lesser curvature, and wherein the second medical name includes a greater curvature.

8. A method of operating a device for setting coordinates of each part of an organ of a human body, the method comprising:

receiving organ information on the organ;

setting a plurality of isolines connecting a first area corresponding to a first part constituting the organ and a second area corresponding to a second part constituting the organ;

generating organ coordinate system information including the organ information and isoline information on the plurality of isolines, wherein the setting comprises:

setting a plurality of first points at equal intervals from a first start point to a first end point on the first area;

assigning sequential numbers to the plurality of first points from the first start point to the first end point;

setting a plurality of second points at equal intervals from a second start point to a second end point on the second area;

assigning sequential numbers to the plurality of second points from the second start point to the second end point; and setting the plurality of isolines by connecting the first points and the second points having the same assigned numbers, wherein the organ coordinate system information is configured to enable a position of the organ to be described in a standardized manner using the plurality of isolines despite differences in shape of the organ among different patients, and wherein the organ information includes a name of the organ and medical names of respective parts constituting the organ.

9. The method of claim 8, wherein the setting of the plurality of isolines includes:

setting a plurality of first points on the first area;

setting a plurality of second points on the second area; and setting the plurality of isoline by connecting the first point and the second point positioned at the same order from starting points to end points of the first area and the second area.

10. The method of claim 9, wherein the plurality of first points are set at equal intervals, wherein the plurality of second points are set at equal intervals, and wherein a number is set to each of the plurality of isolines sequentially from an isoline formed by connecting the starting points to an isoline formed by connecting the end points.

11. The method of claim 10, wherein the setting of the organ coordinate system information includes:

calculating a distance spaced apart from the first point or the second point positioned at the same order on an isoline formed by connecting the first point and the second point positioned at the same order;

acquiring a third point positioned at the distance spaced apart from the first point or the second point positioned at the same order; and generating the organ coordinate system information further including point information representing the plurality of first points, the plurality of second points, and the third point.

12. The method of claim 11, wherein the plurality of isolines are positioned on an inner circumferential surface corresponding to a periphery of the organ.

13. The method of claim 12, wherein the organ information includes an organ image representing the organ.

14. The method of claim 13, wherein the organ information includes a name of the organ and medical names of respective parts constituting the organ, wherein the first part corresponds to a first medical name, wherein the second part corresponds to a second medical name, wherein the organ corresponds to a stomach, wherein the first medical name includes a lesser curvature, and wherein the second medical name includes a greater curvature.

15. A non-transitory computer-readable recording medium coupled to a computer and storing a program for executing the method of claim 8.

* * * * *